United States Patent
Wang et al.

(10) Patent No.: US 12,232,339 B2
(45) Date of Patent: Feb. 18, 2025

(54) NANOMATERIAL, PREPARATION METHOD THEREOF, AND SEMICONDUCTOR DEVICE

(71) Applicant: TCL TECHNOLOGY GROUP CORPORATION, Huizhou (CN)

(72) Inventors: Jin Wang, Huizhou (CN); Yixing Yang, Huizhou (CN)

(73) Assignee: TCL TECHNOLOGY GROUP CORPORATION, Huizhou (CN)

( * ) Notice: Subject to any disclaimer, the term of this patent is extended or adjusted under 35 U.S.C. 154(b) by 376 days.

(21) Appl. No.: 17/838,701

(22) Filed: Jun. 13, 2022

(65) Prior Publication Data
US 2022/0302401 A1   Sep. 22, 2022

Related U.S. Application Data (63) Continuation of application No. PCT/CN2020/138638, filed on Dec. 23, 2020.

(30) Foreign Application Priority Data

Dec. 28, 2019   (CN) .......................... 201911384737.7

(51) Int. Cl.
  *H10K 30/15*   (2023.01)
  *B82Y 30/00*   (2011.01)
  (Continued)

(52) U.S. Cl.
  CPC ............ *H10K 30/152* (2023.02); *B82Y 30/00* (2013.01); *C07C 50/04* (2013.01); *C09K 11/0811* (2013.01)

(58) Field of Classification Search
  CPC .... H10K 30/152; H10K 30/50; H10K 50/115; H10K 50/16; H10K 85/60;
  (Continued)

(56) References Cited

U.S. PATENT DOCUMENTS

2008/0081016 A1* 4/2008 Peng ...................... C01G 51/02
                                                          423/605
2011/0284825 A1   11/2011 Yang et al.
(Continued)

FOREIGN PATENT DOCUMENTS

CN          103429370 A      12/2013
CN          103855307 A       6/2014
(Continued)

OTHER PUBLICATIONS

World Intellectual Property Organization (WIPO) International Search Report for PCT/CN2020/138638 Mar. 23, 2021 4 Pages (Including Translation).

(Continued)

*Primary Examiner* — Douglas W Owens
(74) *Attorney, Agent, or Firm* — ANOVA LAW GROUP, PLLC

(57) ABSTRACT

A nanomaterial includes a ZnO nanocrystal and a surface ligand bonded to the ZnO nanocrystal. The surface ligand has a structure of

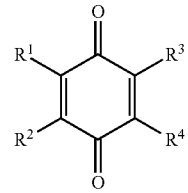

$R^1$, $R^2$, and $R^3$ are independently selected from at least one of an alkyl group, an alkoxy group, a hydroxyalkoxy group, a hydroxyl group, or a hydrogen atom. $R^4$ is selected from a hydrocarbon group having a carbon number of 5 to 60. A (Continued)

carbon number of the alkyl group ranges from 1 to 5. A carbon number of the alkoxy group ranges from 1 to 5. A carbon number of the hydroxyalkoxy group ranges from 1 to 5.

20 Claims, 2 Drawing Sheets

(51) Int. Cl.
    *C07C 50/04* (2006.01)
    *C09K 11/08* (2006.01)

(58) Field of Classification Search
    CPC .. H10K 2102/101; B82Y 30/00; B82Y 10/00; B82Y 40/00; C07C 50/04; C07C 50/28; C09K 11/0811; C09C 1/043; C09C 3/08; Y02E 10/549
    See application file for complete search history.

(56) References Cited

U.S. PATENT DOCUMENTS

| | | | |
|---|---|---|---|
| 2014/0199400 A1 | | 7/2014 | Ogawa et al. |
| 2014/0231717 A1 | | 8/2014 | Sakakibara et al. |
| 2022/0011664 A1* | | 1/2022 | Talapin ............... H10K 50/115 |

FOREIGN PATENT DOCUMENTS

| | | | | |
|---|---|---|---|---|
| CN | 106450021 A | | 2/2017 | |
| CN | 106601926 A | | 4/2017 | |
| CN | 108735906 A | | 11/2018 | |
| CN | 109994620 A | | 7/2019 | |
| CN | 110484233 A | * | 11/2019 | ............ B82Y 20/00 |
| KR | 20170022951 A | | 3/2017 | |
| WO | 2017010398 A1 | | 1/2017 | |
| WO | 2017216570 A1 | | 12/2017 | |
| WO | 2018103747 A1 | | 6/2018 | |
| WO | 2018120513 A1 | | 7/2018 | |

OTHER PUBLICATIONS

Wasiu et al., Dye-modified ZnO nanohybrids: optical properties of the potential solar cell nanocomposites, Int Nano Lett, DOI 10.1007/s40089-017-0211-5.
The European Patent Office (EPO) Supplementary European Search Report for EP20906671 Mar. 28, 2023 5 Pages.
The Patent Office of India Office Action for Application No. 202227043110 Feb. 8, 2023 7 Pages.
Zhang Guishui et al., "Overlooked Role of Carbonyls of Natural Organic Matter on the Dissolution of Zinc Oxide Nanoparticles", ACS Earth and Space Chemistry, vol. 3, No. 12, Nov. 12, 2019, pp. 2786-2794, XP093032157, ISSN: 2472-3452, DOI: 10.1021/acsearthspacechem.9b00253.
Eto Hirozumi et al., "A Novel Solvent Effect in the Practical Synthesis of Ubiquinone-10", Chemistry Letters, vol. 17, No. 10, Oct. 5, 1988, pp. 1597-1600, XP093031598, JP ISSN: 0366-7022, DOI: 10.1246/cl. 1988. 1597.

* cited by examiner

NANOMATERIAL, PREPARATION METHOD THEREOF, AND SEMICONDUCTOR DEVICE

CROSS-REFERENCE TO RELATED APPLICATIONS

The present application is a continuation of International Application No. PCT/CN2020/138638, filed Dec. 23, 2020, which claims priority to Chinese Application No. 201911384737.7 filed Dec. 28, 2019, the entire contents of both of which are incorporated herein by reference.

TECHNICAL FIELD

The present disclosure generally relates to the display technology field and, more particularly, to a nanomaterial, a preparation method of the nanomaterial, and a semiconductor device.

BACKGROUND

A zinc oxide (ZnO) nanocrystal is used as a direct band gap semiconductor material with a band gap of 3.3 eV at room temperature, which has a relatively large band gap and exciton bonding energy. The ZnO nanocrystal has a high electron mobility, high visible light transmittance, and excellent water oxygen stability. An electron transport layer material based on the ZnO nanocrystal has been studied or applied in many electroluminescent devices, such as solar cells, organic light-emitting diodes, and quantum dot light-emitting diodes.

A preparation method of the ZnO nanocrystal is a low-temperature solution synthesis method. However, a defect is easily generated on a surface of the ZnO nanocrystal when the ZnO nanocrystal is synthesized by the low-temperature solution synthesis method. Thus, the electron mobility is low, and the stability is poor when the ZnO nanocrystal is used as an electron transport layer of the electroluminescent device, which significantly affects the efficiency and life of the electroluminescent device. In order to solve this problem, researchers perform ligand modification on the surface of the nanocrystal to passivate the surface defect to improve the stability and electron mobility of the electroluminescent device. Currently, the ligand used to reduce the surface defect of the ZnO nanocrystal mainly includes acetate, hydroxyl, alkyl, or alcohol ether. However, when the obtained ZnO nanocrystal is used as the electron transport layer, the light-emitting efficiency and life of the obtained light-emitting device still cannot meet the requirements of the display industry.

SUMMARY

A purpose of embodiments of the present disclosure is to provide a nanomaterial, a preparation method thereof, and a semiconductor device having the nanomaterial, which aims to solve the problem that the electron mobility is low when the ZnO nanocrystal with the surface defect is used as the electron transport layer of the light-emitting device, and the light-emitting device has low light-emitting efficiency and short life due to the surface defect.

Embodiments of the present disclosure provide a nanomaterial, including a ZnO nanocrystal and a surface ligand bonded to the ZnO nanocrystal. The surface ligand has a structure of

$R^1$, $R^2$, and $R^3$ are independently selected from at least one of an alkyl group, an alkoxy group, a hydroxyalkoxy group, a hydroxyl group, or a hydrogen atom. $R^4$ is selected from a hydrocarbon group having a carbon number of 5 to 60. A carbon number of the alkyl group ranges from 1 to 5. A carbon number of the alkoxy group ranges from 1 to 5. A carbon number of the hydroxyalkoxy group ranges from 1 to 5.

Embodiments of the present disclosure provide a preparation method of a nanomaterial. The method includes providing an initial ZnO nanocrystal solution. A solute of the initial ZnO nanocrystal solution is a ZnO nanocrystal having a first surface ligand. The method further includes preparing a solution of a second surface ligand and mixing the initial ZnO nanocrystal solution and the solution of the second surface ligand to cause a displacement reaction between the first surface ligand on the initial ZnO nanocrystal surface and the second surface ligand to prepare the ZnO nanocrystal with a surface bonded with the second surface ligand. The second surface ligand has a structure of $R^1$, $R^2$, and $R^3$ are independently selected from at least one of an alkyl group, an alkoxy group, a hydroxyalkoxy group, a hydroxyl group, and a hydrogen atom. $R^4$ is selected from a hydrocarbon group having a carbon number of 5 to 60. A carbon number of the alkyl group ranges from 1 to 5. A carbon number of the alkoxy group ranges from 1 to 5. A carbon number of the hydroxyalkoxy group ranges from 1 to 5.

Embodiments of the present disclosure provide a semiconductor device, including an anode, a cathode, an active layer, and an electron transport layer. The anode and the cathode are oppositely to each other. The active layer is between the anode and the cathode. The electron transport layer is between the active layer and the cathode. A material of the electron transport layer including a nanomaterial. The nanomaterial includes a ZnO nanocrystal and a surface ligand bonded to the ZnO nanocrystal. The surface ligand has a structure of $R^1$, $R^2$, and $R^3$ are independently selected from at least one of an alkyl group, an alkoxy group, a hydroxyalkoxy group, a hydroxyl group, and a hydrogen atom. $R^4$ is selected from a hydrocarbon group having a carbon number of 5 to 60. A carbon number of the alkyl group ranges from 1 to 5. A carbon number of the alkoxy group ranges from 1 to 5. A carbon number of the hydroxyalkoxy group ranges from 1 to 5.

According to the nanomaterial of the present disclosure, the electron mobility of the ZnO nanocrystal can be improved, and the stability of the solution can be improved.

DETAILED DESCRIPTION OF THE EMBODIMENTS

In order to make the objectives, technical solutions, and advantages of the present disclosure clearer, the present disclosure is further described in detail below in connection with the accompanying drawings and embodiments. Embodiments described herein are only used to explain the present disclosure and are not intended to limit the present disclosure.

In the description of the present disclosure, a compound and its derivative involved are named according to the International Union of Pure and Applied Chemistry (IUPAC) or Chemical Abstracts Service (CAS, located in Columbus, Ohio). Compound groups involved are described as follows.

"Alkyl" refers to a saturated chain hydrocarbon group having only carbon and hydrogen, which may have a straight carbon chain and/or a branched carbon chain. Alkyl may include, but is not limited to, methyl, ethyl, propyl, isopropyl, butyl, isobutyl, pentyl, isopentyl, etc. A carbon number of the alkyl group may range from 1 to 5. In some embodiments, the carbon number of the alkyl group may be 1, 2, 3, 4, and 5.

"Alkoxy" refers to an alkyl group directly bonded to an oxygen atom and may include, but is not limited to, methoxy, ethoxy, propoxy, butoxy, isobutoxy, tert-butoxy, etc. A carbon number of the alkoxy group may range from 1 to 5. In some embodiments, the carbon number of the alkoxy group may be 1, 2, 3, 4, and 5.

"Hydroxyalkoxy" refers to an alkyl group that is directly bonded to an oxygen atom and has at least one carbon atom that is connected to a hydroxyl group, such as hydroxymethoxy, hydroxyethoxy, hydroxypropoxy, and hydroxybutoxy. A carbon number of the hydroxyalkoxy may range from 1 to 5. In some embodiments, the carbon number of the hydroxyalkoxy may be 1, 2, 3, 4, and 5.

In order to solve the technical problems and make the technical solutions and beneficial effects of the present disclosure clearer, the present disclosure is further described in detail below in connection with embodiments of the present disclosure. Embodiments described here are merely used to explain the present disclosure and are not intended to limit the present disclosure.

Embodiments of the present disclosure provide a nanomaterial. The nanomaterial may include a zinc oxide (ZnO) nanocrystal and a surface ligand bonded to the ZnO nanocrystal. A structure of the surface ligand is shown in Formula 1.

Formula I

In Formula 1, $R^1$, $R^2$, and $R^3$ may each include at least one of an alkyl group, an alkoxy group, a hydroxyalkoxy group, a hydroxyl group, and a hydrogen atom. $R^4$ may include a hydrocarbon group that has a carbon number of 5 to 60. The carbon number of the alkyl group may range from 1 to 5. The carbon number of the alkoxy group may range from 1 to 5. The carbon number of the hydroxyalkoxy group may range from 1 to 5.

In embodiments of the present disclosure, the nanomaterial includes a ZnO nanocrystal and a surface ligand with a benzoquinone structure as shown in Formula 1 that is bonded to the ZnO nanocrystal. The surface ligand contains a long-chain hydrocarbon group having a carbon number of 5 to 60. On one hand, the long-chain hydrocarbon group having a carbon number of 5 to 60 may increase a distance between adjacent ZnO nanocrystals to prevent the ZnO nanocrystal from agglomeration. Thus, the dispersion performance of the ZnO nanocrystal may be improved, and the stability of the ZnO nanocrystal may be optimized. On another hand, with the benzoquinone structure, a defect state caused by a dangling bond and an oxygen vacancy on the surface of the ZnO nanocrystal may be passivated. The oxygen atom of the benzoquinone structure may have good electron acceptance ability and have an affinity to a molecular chain and an entire molecule. Thus, the molecule may become a good electron supply and acceptance carrier, so that the carrier transport and injection ability of the ZnO nanocrystal may be improved. With the benzoquinone structure, the charge blocking that is caused by the long-chain hydrocarbon group may be reduced. The charge blocking may refer to insulating and blocking effect, by the long-chain hydrocarbon group on the surface of the ZnO nanocrystal, on the electron transport between the adjacent nanocrystals. The electron mobility of the ZnO crystal may be increased. In addition, due to the excellent hydrophobicity of the alkyl chain in the surface ligand molecule, the internal ZnO nanocrystal material may be protected from oxygen and water to a certain degree after the surface ligand is bonded at the surface of the ZnO nanocrystal. Thus, the stability of the device may be improved. In summary, the nanomaterial and the surface ligan of the ZnO nanocrystal of embodiments of the present disclosure may improve the electron mobility of the ZnO nanocrystal and improve the stability of the solution.

In some embodiments, the nanomaterial may include the ZnO nanocrystal and the surface ligand bonded to the ZnO nanocrystal.

In some embodiments, $R^4$ may include a saturated or unsaturated hydrocarbon group having 5 to 30 carbon atoms. When the carbon number of $R^4$ is 5 to 30, the surface ligand of the benzoquinone structure may have a suitable chain length. The distance between the adjacent ZnO nanocrystals may be increased, and the ZnO crystal may be prevented from agglomeration. Thus, the dispersion performance of the ZnO nanocrystal may be improved, and the stability of the solution of the ZnO nanocrystal may be improved. Moreover, the insulating and blocking effect caused by the introduction of the long-chain group to the charge transport between the adjacent nanocrystals may be reduced. Thus, the electron mobility of the ZnO nanocrystal may be significantly improved. In addition, the alkyl chain may have excellent hydrophobicity. After the surface ligand is bonded on the surface of the ZnO nanocrystal, the internal ZnO nanocrystal material may be protected from oxygen and water to a certain degree to improve the stability of the device.

In embodiments of the present disclosure, $R^1$, $R^2$, and $R^3$ may each independently include at least one of an alkyl group, an alkoxy group, a hydroxyalkoxy group, a hydroxyl group, or a hydrogen atom. The alkyl group may be represented as —R. The alkoxy group may be represented as —OR. The hydroxyalkoxy group may be represented as —OROH. R may be the alkyl group. The alkyl chain introduced by $R^4$ may have a relatively long-chain length and excellent hydrophobicity. After $R^4$ is bonded to the surface of the ZnO nanocrystal, the internal ZnO nanocrystal material may be protected from oxygen and water to a certain degree to improve the stability of the device.

In some embodiments, the alkyl group may include a straight-chain saturated alkyl group having 1 to 5 carbon atoms. At least one of $R^1$, $R^2$, or $R^3$ may include the straight-chain saturated alkyl group having 1 to 5 carbon atoms. Thus, by protecting the internal ZnO nanocrystal material from oxygen and water to a certain degree, the insulating and blocking effect on the charge transport between adjacent nanocrystals caused by an excessive long chain length may be avoided.

In some embodiments, the alkoxy group may include a straight-chain saturated alkoxy group having 1 to 4 carbon atoms. At least one of $R^1$, $R^2$, or $R^3$ includes the straight-chain saturated alkoxy group having 1 to 4 carbon atoms. Thus, by protecting the internal ZnO nanocrystal material from oxygen and water to a certain degree, the insulating and blocking effect on the charge transport between adjacent nanocrystals caused by an excessive long chain length may be avoided.

In some embodiments, the hydroxyalkoxy group may include a straight-chain saturated hydroxyalkoxy group having 1 to 3 carbon atoms. At least one of $R^1$, $R^2$, or $R^3$ may include the straight-chain saturated group having 1 to 3 carbon atoms. Thus, by protecting the internal ZnO nanocrystal material from oxygen and water to a certain degree, the insulating and blocking effect on the charge transport between adjacent nanocrystals caused by an excessive long chain length may be avoided.

In some embodiments, a total carbon number of $R^1$ and $R^2$ may be less than 6. The carbon number of $R^3$ may be less than 3. Thus, in the obtained structure of Formula 1, the steric hindrance may be small, and the insulating and blocking effect on the charge transport between the adjacent nanocrystals may be minimum.

In some embodiments, the surface ligand may include at least one of the following structures.

-continued

The surface ligand may have an efficient carrier transport and injection ability. With the surface ligand, the defect on the surface of the ZnO nanocrystal may be passivated. In addition, the hydrocarbyl chain in the ligand molecule may have excellent hydrophobicity and have a shielding effect on water and oxygen. Thus, the stability of the ZnO nanocrystal and the adjacent thin-film layers in the device may be improved.

In some embodiments, in the nanomaterial, a molar ratio of the ZnO nanocrystal to a surface ligand bonded to the ZnO nanocrystal may range from 1:5 to 1:100. With the molar ratio of the ZnO nanocrystal to the surface ligand bonded at the ZnO nanocrystal being in that range, the surface ligand may be sufficiently bonded to a reaction site on the ZnO nanocrystal to improve the stability of the ZnO nanocrystal, reduce the surface defect on the ZnO nanocrystal, and improve the electron transport performance of the ZnO nanocrystal. When a molar content of the surface ligand bonded to the ZnO nanocrystal is too high, for example, when a molar amount of the ZnO nanocrystal is 1 and the molar content of the surface ligand exceeds 100, the bonding of the surface ligand to the ZnO nanocrystal may not be strong enough, and hence the surface ligand may easily fall off to affect the electron transport performance of the nanomaterial. When the molar content of the surface ligand bonded to the ZnO nanocrystal is too low, for example, when the molar content of the ZnO nanocrystal is 1, and the molar content of the surface ligand is less than 5, the surface ligand may have a limited effect on the stability of the ZnO nanocrystal and the electron transport layer, and hence cannot significantly improve the ZnO nanocrystal.

The nanomaterial of embodiments of the present disclosure may be prepared by the following method.

Figure 1:
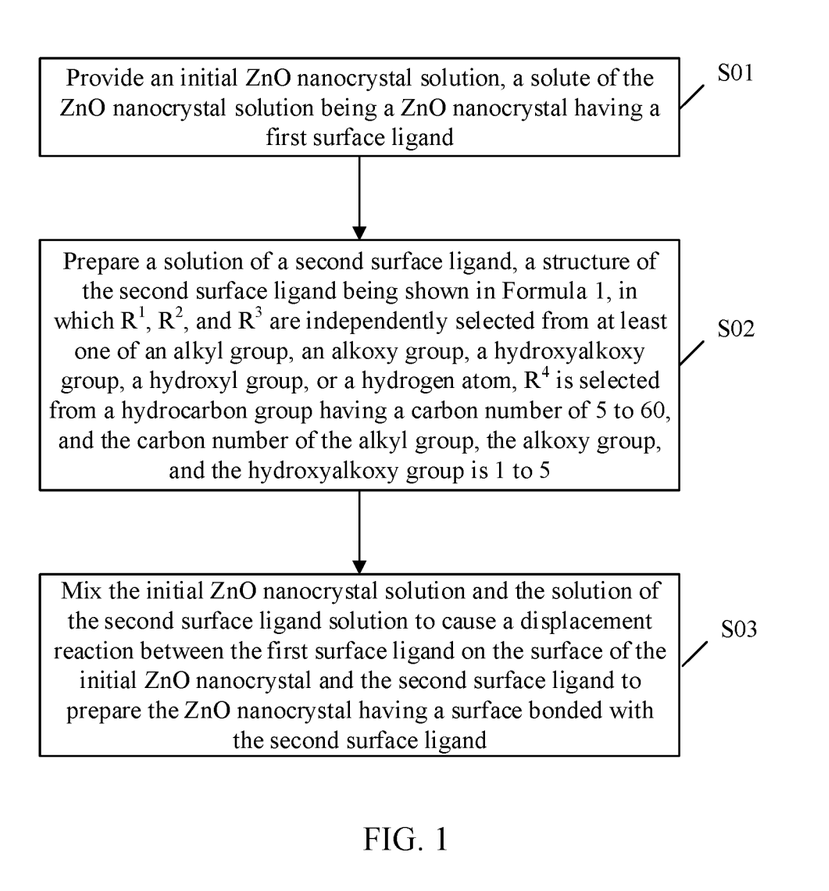
FIG. 1 is a schematic flowchart of a preparation process of a nanomaterial according to some embodiments of the present disclosure.

The present disclosure also provides a preparation method of a nanomaterial, including:

providing an initial ZnO nanocrystal solution, a solute of the ZnO nanocrystal solution being a ZnO nanocrystal having a first surface ligand (S01);

preparing a solution of a second surface ligand, a structure of the second surface ligand being shown in Formula 1, in which $R^1$, $R^2$, and $R^3$ each include at least one of an alkyl group, an alkoxy group, a hydroxyalkoxy group, a hydroxyl group, or a hydrogen atom, $R^4$ includes a hydrocarbon group having a carbon number of 5 to 60, and the carbon number of the alkyl group, the alkoxy group, and the hydroxyalkoxy group is 1 to 5 (S02);

Formula I mixing the initial ZnO nanocrystal solution and the solution of the second surface ligand solution to cause a displacement reaction between the first surface ligand on the surface of the initial ZnO nanocrystal and the second surface ligand to prepare the ZnO nanocrystal having a surface bonded with the second surface ligand (S03).

In the preparation method of the nanomaterial of embodiments of the present disclosure, the initial ZnO nanocrystal solution and the surface ligand solution may only need to be mixed to cause the displacement reaction between the first surface ligand on the surface of the initial ZnO nanocrystal and the second surface ligand. Thus, the ZnO nanocrystal with the surface bonded with the second surface ligand may be prepared. The method may have a simple process and a mild condition. With the method, large-scale production may be easily realized. Most importantly, with the nanomaterial prepared by the method, the electron mobility of the ZnO nanocrystal and the solution stability may be improved.

In some embodiments, at S01, the initial ZnO nanocrystal solution may be prepared using, e.g., a solution method. The solute of the ZnO nanocrystal solution may be the ZnO nanocrystal having the first surface ligand. In some embodiments, the first surface ligand may include at least one of an acetate ligand, a hydroxyl ligand, an alkyl ligand, or an alcohol ether ligand. In some embodiments, the first surface ligand may include an acetate ligand and/or a hydroxyl ligand. By selecting the initial ZnO nanocrystal having the acetate ligand and/or the hydroxyl ligand, a ligand replacement rate may be improved in the subsequent ligand replacement reaction with the second surface ligand, and the first surface ligand on the surface of the initial ZnO nanocrystalline may be sufficiently replaced with the second surface ligand.

At S02, the solution of the second surface ligand is prepared. The selection of the second surface ligand is described above, which is not repeated here. In some embodiments, in the second organic ligand shown in Formula 1, $R^4$ may include a saturated or unsaturated hydrocarbon group having a carbon number of 5 to 30. In embodiments of the present disclosure, in the first organic ligand shown in Formula 1, $R^1$, $R^2$, and $R^3$ may each include at least one of an alkyl group, an alkoxy group, a hydroxyalkoxy group, a hydroxyl group, or a hydrogen atom. In some embodiments, the alkyl group may include the straight-chain saturated alkyl group having 1 to 5 carbon atoms. In some embodiments, the alkoxy group may include the straight-chain saturated alkoxy group having 1 to 4 carbon atoms. In some embodiments, in the first organic ligand shown in Formula 1, $R^1$, $R^2$, and $R^3$ may each include at least one of an alkyl group, an alkoxy group, a hydroxyalkoxy group, a hydroxyl group, or a hydrogen atom. The hydroxyalkoxy group may include the straight-chain saturated hydroxyalkoxy group having 1 to 3 carbon atoms. In some embodiments, in the first organic ligand shown in Formula 1, at least one of $R^1$, $R^2$, or $R^3$ may include a hydroxyl group or a hydrogen atom.

In some embodiments, in the first organic ligand shown in Formula 1, the first surface ligand may include at least one of the following structures.

The first surface ligand may have the efficient carrier transport and injection ability. The first surface ligand may be used to passivate the defect on the surface of the ZnO nanocrystal. In addition, the hydrocarbyl chain in the ligand molecule may have excellent hydrophobicity and have a shielding effect on water and oxygen. With the ligand, the stability of the ZnO nanocrystal and the adjacent thin film layers in the device may be improved.

At S03, the initial ZnO nanocrystal solution is mixed with the solution of the second surface ligand to cause the displacement reaction between the first surface ligand on the surface of the initial ZnO nanocrystal and the second surface ligand to prepare the ZnO nanocrystal with the surface bonded with the second surface ligand.

In some embodiments, in mixing the initial ZnO nanocrystal solution and the solution of the second surface ligand, the initial ZnO nanocrystal solution and the second surface ligand solution may be mixed according to a molar ratio of the ZnO nanocrystal to the second surface ligand that ranges from 1:5 to 1:100. With the molar ratio of the initial ZnO nanocrystal to the second surface ligand being within the above range, the second surface ligand may fully replace the first surface ligand on the initial ZnO nanocrystal to form the ZnO nanocrystal bonded with the second surface ligand to improve the stability of the ZnO nanocrystal, reduce the surface defect of the ZnO nanocrystal, and improve the electron transport performance. When the molar content of the surface ligand bonded to the ZnO nanocrystal is too high, for example, when a molar amount of the ZnO nanocrystal is 1 and the molar content of the surface ligand exceeds 100, the bonding of the surface ligand to the ZnO nanocrystal may not be strong enough. The surface ligand may easily fall off to affect the electron transport performance of the nanomaterial. When the molar content of the surface ligand bonded to the ZnO nanocrystal is too low, for example, when the molar content of the ZnO nanocrystal is 1 and the molar content of the surface ligand is less than 5, the surface ligand may not be enough to replace the first surface ligand of the initial ZnO nanocrystal and may not effectively improve the stability of the ZnO nanocrystal and the electron transport layer.

In some embodiments, in mixing the initial ZnO nanocrystal solution and the solution of the second surface ligand, the mixed solution system may react at a temperature of 50° C. to 250° C. for 20 min to 40 min. If the reaction temperature is too low or the reaction time is too short, the first surface ligand of the initial ZnO nanocrystal may not sufficiently be displaced with the second surface ligand. If the reaction temperature is too high or the reaction time is too long, the second surface ligand may easily be caused to decompose. Thus, the property of the surface ligand bonded to the ZnO nanocrystal may be affected. The purpose of modifying the ZnO nanocrystal may be changed, and even the stability and the electron transport performance of the ZnO nanocrystal may be further reduced.

Figure 2:
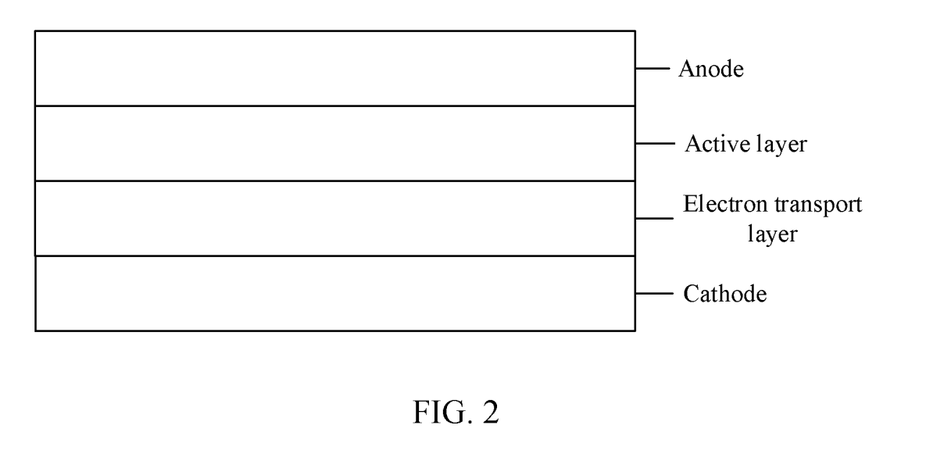
FIG. 2 is a schematic structural diagram of a semiconductor device according to some embodiments of the present disclosure.

As shown in FIG. 2, the present disclosure also provides a semiconductor device, including an anode, a cathode, an active layer, and an electron transport layer. The anode and the cathode are arranged oppositely to each other. The active layer is arranged between the anode and the cathode. The electron transport layer is arranged between the active layer and the cathode. A material of the electron transport layer is a nanomaterial. The nanomaterial includes a ZnO nanocrystal and a surface ligand bonded to the ZnO nanocrystal. The structure of the surface ligand is shown in Formula I.

Formula I

In Formula I, $R^1$, $R^2$, and $R^3$ may each include at least one of an alkyl group, an alkoxy group, a hydroxyalkoxy group, a hydroxyl group, or a hydrogen atom. $R^4$ may include a hydrocarbon group having a carbon number of 5 to 60. The carbon number of the alkyl group, the alkoxy group, and the hydroxyalkoxy group may range from 1 to 5.

In the semiconductor device of embodiments of the present disclosure, the nanomaterial may be used as the electron transport layer. Therefore, the obtained semiconductor device may have relatively good photoelectric efficiency and relatively good stability.

In some embodiments, the nanomaterial may include the ZnO nanocrystal and the surface ligand bonded to the ZnO nanocrystal.

The material of the electron transport layer is the nanomaterial. The surface ligand of the nanomaterial is as shown in Formula I. In some embodiments, in the second organic ligand shown in Formula I, $R^4$ may include a saturated or unsaturated hydrocarbon group having 5 to 30 carbon atoms. In embodiments of the present disclosure, in the first organic ligand shown in Formula I, $R^1$, $R^2$, and $R^3$ may each include at least one of an alkyl group, an alkoxy group, a hydroxyalkoxy group, a hydroxyl group, or a hydrogen atom. In some embodiments, the alkyl group may include the straight-chain saturated alkyl group having 1 to 5 carbon atoms. In some embodiments, the alkoxy group may include the straight-chain saturated alkoxy group having 1 to 4 carbon atoms. In some embodiments, in the first organic ligand shown in Formula I, $R^1$, $R^2$, and $R^3$ may each include at least one of an alkyl group, an alkoxy group, a hydroxyalkoxy group, a hydroxyl group, or a hydrogen atom. The hydroxyalkoxy group may include the straight-chain saturated hydroxyalkoxy group having 1 to 3 carbon atoms. In some embodiments, in the first organic ligand shown in Formula I, at least one of $R^1$, $R^2$, or $R^3$ may include the hydroxyl group or the hydrogen atom. In some embodiments, the surface ligand may include at least one of the following structures.

-continued

The surface ligand may have the efficient carrier transport and injection ability. With the surface ligand, the defect on the surface of the ZnO nanocrystal may be passivated. In addition, the hydrocarbyl chain in the ligand molecule may have excellent hydrophobicity and have a shielding effect on water and oxygen. Thus, the stability of the ZnO nanocrystal and the adjacent thin-film layers in the device may be improved.

In some embodiments, the molar ratio of the ZnO nanocrystal to the surface ligand bonded to the ZnO nanocrystal may range from 1:5 to 1:100.

In some embodiments, the semiconductor device may include a solar cell (the device absorbs light from the active layer, such as a perovskite solar cell) or a light-emitting device (the device emits light from a top electrode or a bottom electrode, and the active layer is the light-emitting layer). In some embodiments, the light-emitting device may include an organic light-emitting diode or a quantum dot light-emitting diode. The quantum dot light-emitting diode may include a perovskite light-emitting diode.

The light-emitting device of embodiments of the present disclosure may be a forward structure electroluminescent device or an inverted structure electroluminescent device. The forward structure refers to a structure of substrate/anode/active layer/electron transport layer/cathode. The device having a forward structure may further optionally include one or more hole functional layers, such as a hole injection layer, a hole transport layer, and/or an electron blocking layer, that is arranged between the anode and the quantum dot light-emitting layer. The device having a forward structure may also further optionally include an electron transport layer, an electron injection layer, and/or a hole blocking layer, that is arranged between the electron transport layer and the cathode. The inverted structure is opposite to the forward structure.

In some embodiments, the selection of the anode may not be strictly limited. The anode may include, but is not limited to, an indium-doped tin oxide (ITO).

The material of the active layer may include a quantum dot or organic light-emitting material.

The cathode may include, for example, metal copper, metal silver, or metal aluminum.

The material of the hole injection layer may include one of, but is not limited to, poly(3,4-ethylenedioxythiophene)-polystyrene sulfonic acid (PEDOT:PSS) or a derivative (PEDOT:PSS:s-MoO$_3$) of PEDOT:PSS doped with s-MoO$_3$.

The material of the hole transport layer may include, but is not limited to, poly [(9,9-dioctylfluorenyl-2,7-diyl)-co-(4,4'-(N-(4-sec-butylphenyl)diphenylamine)] (TFB) or poly(9-vinylcarbazole) (PVK).

The material of the electron transport layer may include, but is not limited to, ZnO or titanium oxide (TiO$_2$).

In some embodiments, the light-emitting device may further include a packaging layer. The packaging layer may be arranged on the surface of the top electrode (the electrode away from the substrate) or may be arranged on the surface of the entire electroluminescent device. Examples and comparative examples are described below.

Example 1

An electroluminescent diode device may include an anode, a cathode, an active layer, and an electron transport layer. The anode and the cathode may be arranged oppositely to each other. The active layer may be arranged between the anode and the cathode. The electron transport layer may be arranged between the active layer and the cathode. The anode may be an ITO. The cathode may be made of silver. The active layer may be CdSe@ZnS. The material of the electron transport layer may be the nanomaterial. The nanomaterial may include a ZnO nanocrystal and a surface ligand bonded to the ZnO nanocrystal. The structure of the surface ligand is shown in Formula II.

Formula II

Example 2

An electroluminescent diode device may include an anode, a cathode, an active layer, and an electron transport layer. The anode and the cathode may be arranged oppositely to each other. The active layer may be arranged between the anode and the cathode. The electron transport layer may be arranged between the active layer and the cathode. The anode may include an ITO. The material of the cathode may include silver. The active layer may be CdSe@ZnS. The material of the electron transport layer may include a nanomaterial. The nanomaterial may include a ZnO nanocrystal and a surface ligand bonded to the ZnO nanocrystal. The structure of the surface ligand is shown in Formula III.

Formula III

Example 3

An electroluminescent diode device may include an anode, a cathode, an active layer, and an electron transport layer. The anode and the cathode may be arranged oppositely to each other. The active layer may be arranged between the anode and the cathode. The electron transport layer may be arranged between the active layer and the cathode. The anode may include an ITO. The material of the cathode may include silver. The active layer may be CdSe@ZnS. The material of the electron transport layer may include a nanomaterial. The nanomaterial may include a ZnO nanocrystal and a surface ligand bonded to the ZnO nanocrystal. The structure of the surface ligand is shown in Formula IV.

Formula IV

Comparative Example 1

An electroluminescent diode device may include an anode, a cathode, an active layer, and an electron transport layer. The anode and the cathode may be arranged oppositely to each other. The active layer may be arranged between the anode and the cathode. The electron transport layer may be arranged between the active layer and the cathode. The anode may include an ITO. The material of the cathode may include silver. The active layer may be the CdSe@ZnS quantum dot light-emitting layer. The material of the electron transport layer may include a nanomaterial. The nanomaterial may include a ZnO nanocrystal and a hydroxyl ligand bonded to the ZnO nanocrystal.

The efficiency tests are performed on the electroluminescent diode devices of Examples 1 to 3 and Comparative Example 1. The stability of the devices may be monitored. The devices are packaged under a same condition. By isolating the influence of the external environment on the devices, the external quantum efficiency (EQE) from day 1 to day 90 may be monitored after the devices are packaged. The EQE may be measured by an EQE optical test device.

The test results are shown in Table 1.

TABLE 1

| Item | External Quantum Efficiency (EQE)/(%) | | | | |
|---|---|---|---|---|---|
| Group | Day 1 | Day 10 | Day 30 | Day 60 | Day 90 |
| Comparative Example 1 | 5.6 | 5.8 | 4.9 | 3.7 | 3.0 |
| Example 1 | 8.7 | 8.4 | 8.2 | 8.1 | 7.9 |
| Example 2 | 9.3 | 9.5 | 9.2 | 9.1 | 9.0 |
| Example 3 | 9.3 | 9.2 | 8.9 | 9.2 | 8.7 |

As shown in Table 1, the EQE of the electroluminescent diode devices of Examples 1 to 3 of the present disclosure is significantly improved compared with Comparative Example 1. The stability of the device efficiency in 90 days is maintained at 90% or above (the percentage of a ratio between the EQE of day 90 and the EQE of day 1). Thus, with the selected ligand of the present disclosure, the electron mobility and the stability of the ZnO nanocrystal may be improved to improve the light-emitting efficiency and the device stability of the electroluminescent devices.

The above are merely some embodiments of the present disclosure and are not intended to limit the present disclosure. For those skilled in the art, various modifications and changes may be made to the present disclosure. Any modifications, equivalent replacements, and improvements within the spirit and principle of the present application should be within the scope of the claims of the present application.

What is claimed is:

1. A nanomaterial comprising:
   a ZnO nanocrystal; and
   a surface ligand bonded to the ZnO nanocrystal, the surface ligand having a structure of wherein:
   $R^1$, $R^2$, and $R^3$ are independently selected from at least one of an alkyl group, an alkoxy group, a hydroxyalkoxy group, a hydroxyl group, or a hydrogen atom;
   $R^4$ is selected from a hydrocarbon group having a carbon number of 5 to 60;
   a carbon number of the alkyl group ranges from 1 to 5;
   a carbon number of the alkoxy group ranges from 1 to 5; and
   a carbon number of the hydroxyalkoxy group ranges from 1 to 5.

2. The nanomaterial according to claim 1, wherein the nanomaterial is composed of the ZnO nanocrystal and the surface ligand bonded to the ZnO nanocrystal.

3. The nanomaterial according to claim 1, wherein:
   $R^4$ is selected from a saturated or unsaturated hydrocarbon group having 5 to 30 carbon atoms;
   a total carbon number of $R^1$ and $R^2$ is less than 6; and
   a carbon number of $R^3$ is less than 3.

4. The nanomaterial according to claim 1, wherein:
   the alkyl group is selected from a straight-chain saturated alkyl group having 1 to 5 carbon atoms;
   the alkoxy group is selected from a straight-chain saturated alkoxy group having 1 to 4 carbon atoms; or
   the hydroxyalkoxy group is selected from a straight-chain saturated hydroxyalkoxy group having 1 to 3 carbon atoms.

5. The nanomaterial according to claim 1, wherein the surface ligand is selected from at least one of structures of -continued -continued

6. The nanomaterial according to claim 1, wherein a molar ratio of the ZnO nanocrystal to the surface ligand ranges from 1:5 to 1:100.

7. A preparation method of a nanomaterial comprising:
providing an initial ZnO nanocrystal solution, a solute of the initial ZnO nanocrystal solution including a ZnO nanocrystal having a first surface ligand;
preparing a solution of a second surface ligand, the second surface ligand having a structure of wherein:
$R^1$, $R^2$, and $R^3$ are independently selected from at least one of an alkyl group, an alkoxy group, a hydroxyalkoxy group, a hydroxyl group, or a hydrogen atom;
$R^4$ is selected from a hydrocarbon group having a carbon number of 5 to 60;
a carbon number of the alkyl group ranges from 1 to 5;
a carbon number of the alkoxy group ranges from 1 to 5; and
a carbon number of the hydroxyalkoxy group ranges from 1 to 5; and
mixing the initial ZnO nanocrystal solution and the solution of the second surface ligand to cause a displacement reaction between the first surface ligand on the initial ZnO nanocrystal surface and the second surface ligand to prepare the ZnO nanocrystal with a surface bonded with the second surface ligand.

8. The method according to claim 7, wherein:
$R^4$ is selected from a saturated or unsaturated hydrocarbon group having 5 to 30 carbon atoms;
a total carbon number of $R^1$ and $R^2$ is less than 6; and
a carbon number of $R^3$ is less than 3.

9. The method according to claim 7, wherein:
the alkyl group is selected from a straight-chain saturated alkyl group having 1 to 5 carbon atoms;
the alkoxy group is selected from a straight-chain saturated alkoxy group having 1 to 4 carbon atoms; or
the hydroxyalkoxy group is selected from a straight-chain saturated hydroxyalkoxy group having 1 to 3 carbon atoms.

10. The method according to claim 7, wherein the surface ligand is selected from at least one of structures of -continued

11. The method according to claim 7, wherein mixing the initial ZnO nanocrystal solution and the solution of the second surface ligand includes mixing the initial ZnO nanocrystal solution and the first surface ligand solution according to a molar ratio of the ZnO nanocrystal to the second surface ligand ranging from 1:5 to 1:100.

12. The method according to claim 7, wherein the first surface ligand is selected from at least one of an acetate ligand, a hydroxyl ligand, an alkyl ligand, or an alcohol ether ligand.

13. The method according to claim 12, wherein the first surface ligand is selected from the acetate ligand or hydroxyl ligand.

14. The method according to claim 7, wherein mixing the initial ZnO nanocrystal solution and the solution of the second surface ligand includes allowing a mixed solution system of the initial ZnO nanocrystal solution and the solution of the second surface ligand to react at a temperature of 50° C. to 250° C. for 20 min to 40 min.

15. A semiconductor device comprising:
an anode and a cathode opposite to each other;
an active layer between the anode and the cathode; and
an electron transport layer between the active layer and the cathode, a material of the electron transport layer including a nanomaterial, the nanomaterial including a ZnO nanocrystal and a surface ligand bonded to the ZnO nanocrystal, and the surface ligand having a structure of wherein:
R$^1$, R$^2$, and R$^3$ are independently selected from at least one of an alkyl group, an alkoxy group, a hydroxyalkoxy group, a hydroxyl group, or a hydrogen atom;
R$^4$ is selected from a hydrocarbon group having a carbon number of 5 to 60;
a carbon number of the alkyl group ranges from 1 to 5;
a carbon number of the alkoxy group ranges from 1 to 5; and
a carbon number of the hydroxyalkoxy group ranges from 1 to 5.

16. The nanomaterial according to claim 15, wherein the nanomaterial is composed of the ZnO nanocrystal and the surface ligand bonded to the ZnO nanocrystal.

17. The semiconductor device according to claim 15, wherein:
R$^4$ is selected from a saturated or unsaturated hydrocarbon group having 5 to 30 carbon atoms;
a total carbon number of R$^1$ and R$^2$ is less than 6; and
a carbon number of R$^3$ is less than 3.

18. The semiconductor device according to claim 15, wherein:
the alkyl group is selected from a straight-chain saturated alkyl group having 1 to 5 carbon atoms;
the alkoxy group is selected from a straight-chain saturated alkoxy group having 1 to 4 carbon atoms; or
the hydroxyalkoxy group is selected from a straight-chain saturated hydroxyalkoxy group having 1 to 3 carbon atoms.

19. The semiconductor device according to claim 15, wherein the surface ligand includes at least one of structures of -continued 20. The nanomaterial according to claim 15, wherein a molar ratio of the ZnO nanocrystal to the surface ligand ranges from 1:5 to 1:100.

* * * * *